United States Patent [19]

Iida et al.

[11] Patent Number: 5,191,878
[45] Date of Patent: Mar. 9, 1993

[54] ENDOSCOPE DEVICE

[75] Inventors: Yoshihiro Iida, Tama; Jin Kira, Tokyo; Yutaka Ohshima, Hachioji; Toshiyuki Takara, Higashimurayama; Koji Yamaya, Hachioji, all of Japan

[73] Assignee: Olympus Optical Co., Ltd., Tokyo, Japan

[21] Appl. No.: 682,739

[22] Filed: Apr. 9, 1991

[30] Foreign Application Priority Data

| Apr. 12, 1990 | [JP] | Japan | 2-39839[U] |
| Apr. 25, 1990 | [JP] | Japan | 2-107547 |
| Aug. 22, 1990 | [JP] | Japan | 2-221681 |
| Oct. 26, 1990 | [JP] | Japan | 2-286979 |

[51] Int. Cl.⁵ ............................................. A61B 1/00
[52] U.S. Cl. .................................................. 128/4
[58] Field of Search ................................... 128/4, 6

[56] References Cited

U.S. PATENT DOCUMENTS

| 3,841,330 | 10/1974 | Storz . |
| 4,423,727 | 1/1984 | Widran et al. . |
| 4,795,424 | 1/1989 | Burner . |
| 4,820,265 | 4/1989 | DeSatnick et al. . |
| 4,836,187 | 6/1989 | Iwakoshi et al. . |
| 4,841,952 | 6/1989 | Sato et al. ........................... 128/4 |
| 4,860,731 | 8/1989 | Matsuura ............................ 128/4 |
| 4,893,634 | 1/1990 | Kulik et al. . |
| 5,022,382 | 6/1991 | Ohshoji et al. ...................... 128/4 |

FOREIGN PATENT DOCUMENTS

| 53-36633 | 6/1978 | Japan . |
| 61-73634 | 4/1986 | Japan . |
| 61-141340 | 6/1986 | Japan . |
| 1-229221 | 9/1989 | Japan . |

Primary Examiner—Gene Mancene
Assistant Examiner—Thomas Price
Attorney, Agent, or Firm—Frishauf, Holtz, Goodman & Woodward

[57] ABSTRACT

An endoscope device has an endoscope provided with a front end portion where a nozzle and a sucking opening are formed. A first passage and a fluid supply pump are connected to the nozzle to supply fluid to it. A second passage and a suction pump are connected to the sucking opening. Connected to the first and second passages are a third passage and a pump for circulating the fluid in such a way that it is sucked through the sucking opening and jetted through the nozzle.

13 Claims, 15 Drawing Sheets

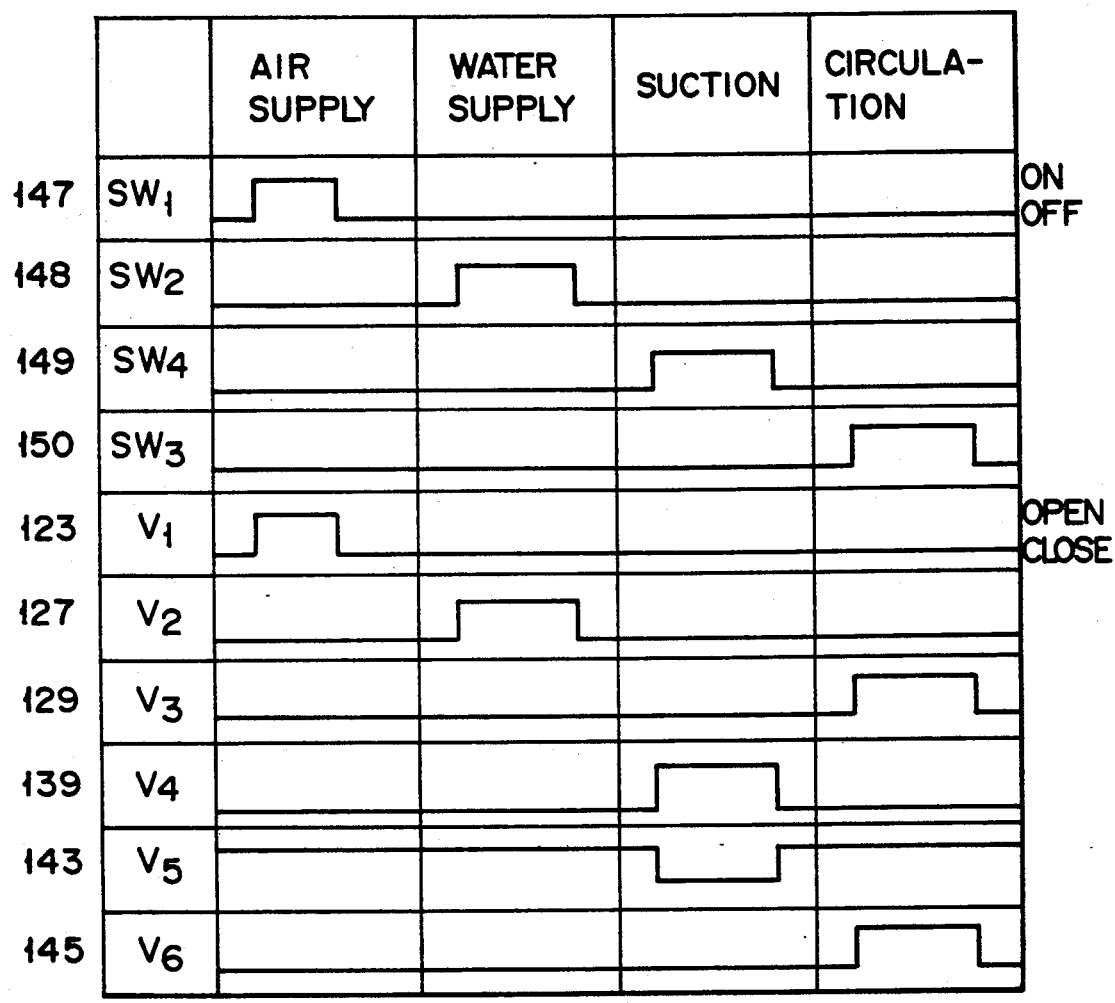
F I G. 5

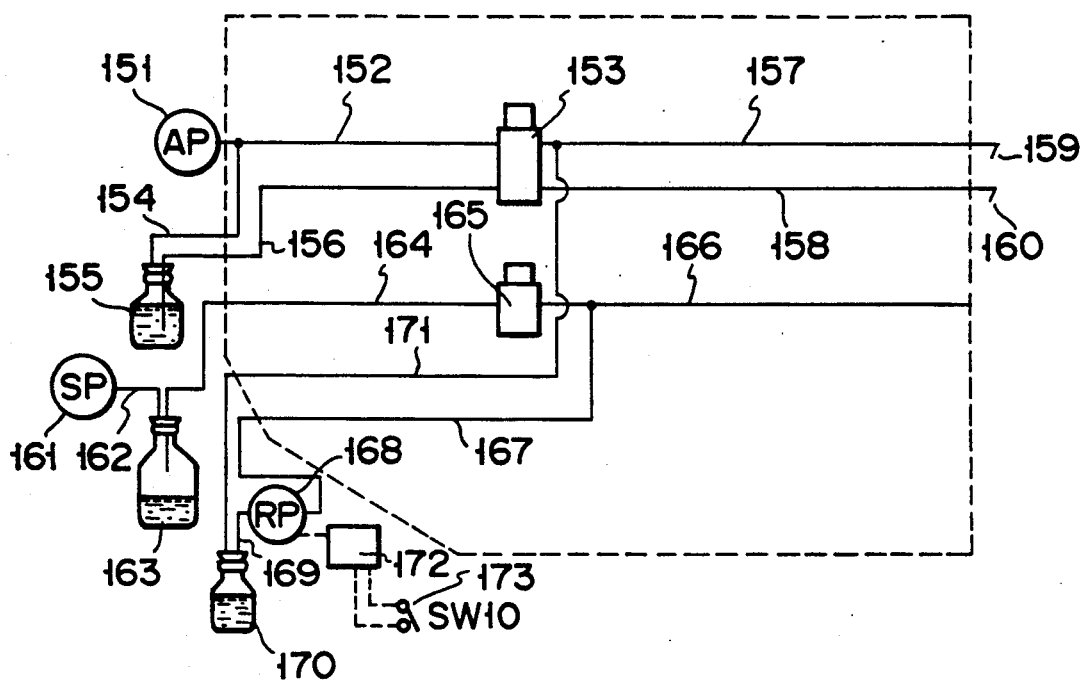
F I G. 6
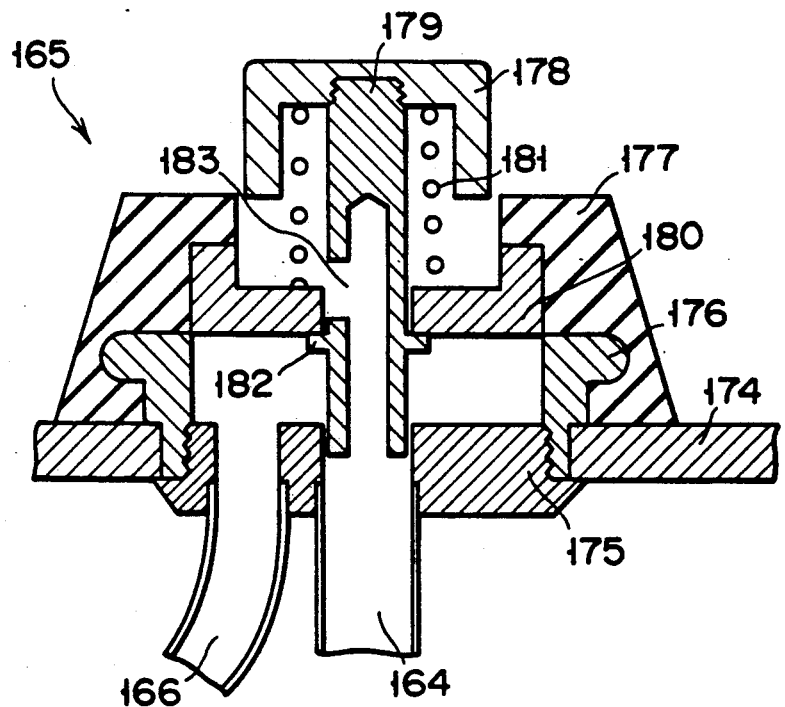
F I G. 7

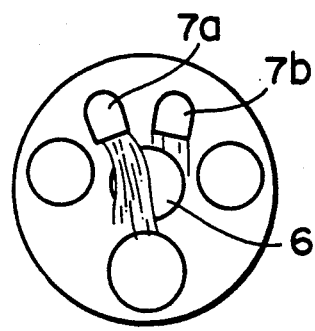
F I G. 10
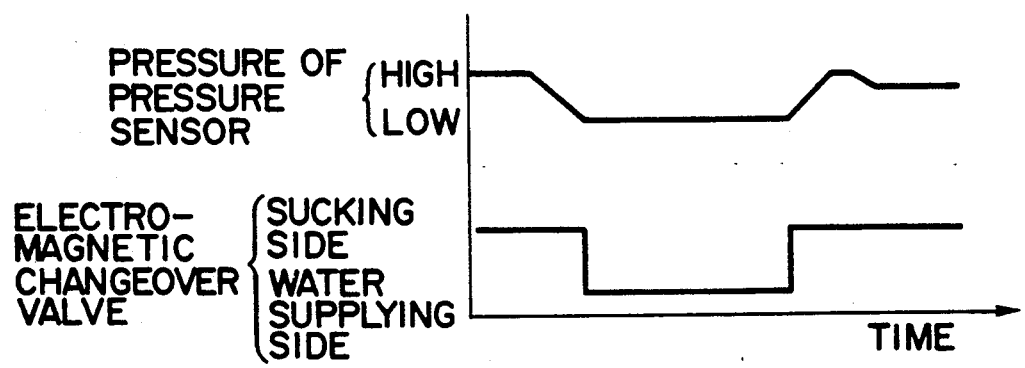
F I G. 14

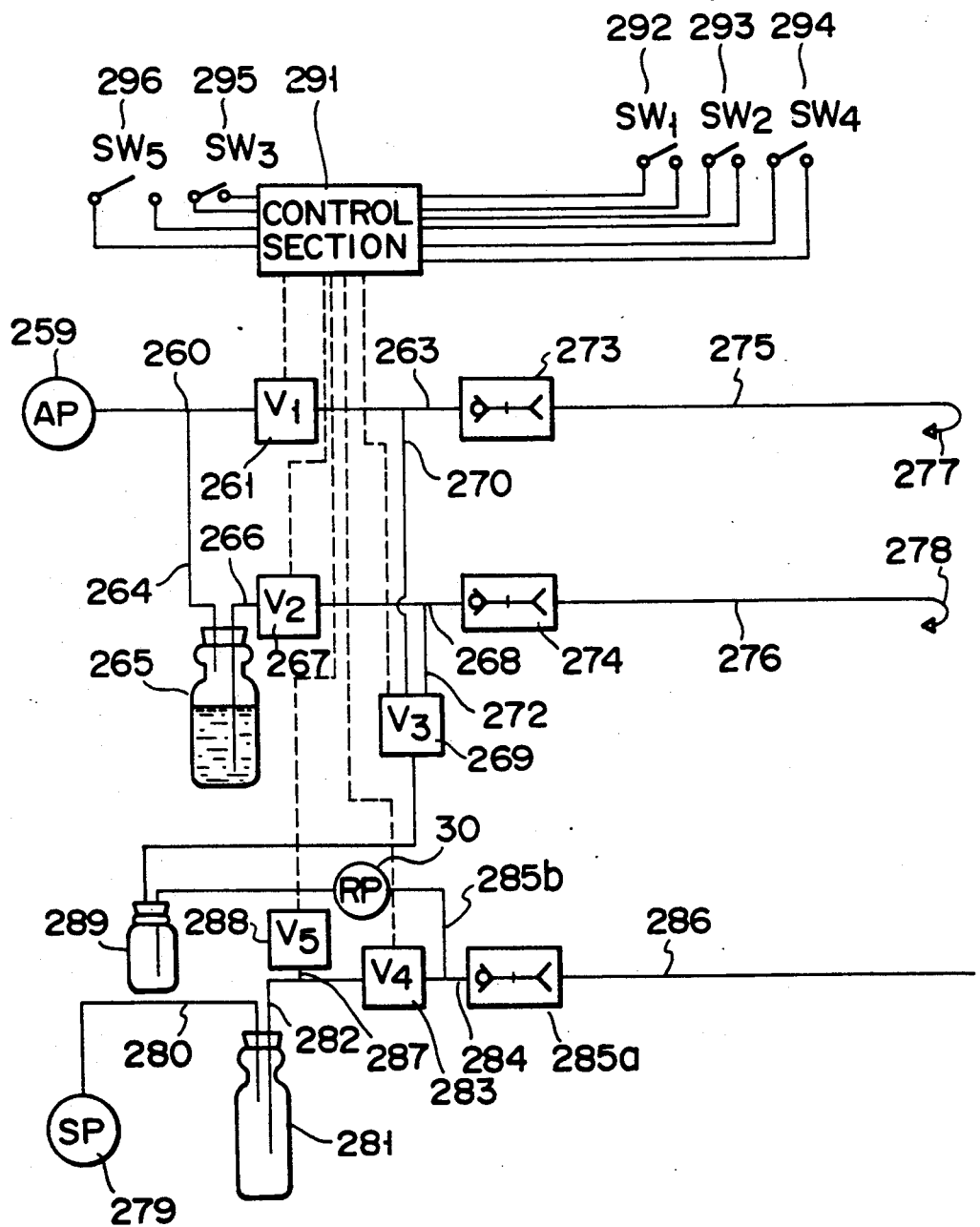
F I G. 11

ENDOSCOPE DEVICE

BACKGROUND OF THE INVENTION

1. Field of the Invention

The present invention relates to an endoscope device having pumps located in an endoscope to make the amount of gas supplied under pressure equal to that of gas sucked under pressure.

2. Description of the Related Art

Conventionally, a nozzle for cleaning a viewing window is formed in the front end portion of the endoscope and gas or fluid is jetted through the nozzle connected to air and water supply pipe systems to clean the viewing window.

In the case of the above-mentioned nozzle, however, matters such as viscous liquid and blood in the cavity of a human body enter into the nozzle and adhere there to thereby making it difficult for air and water to be supplied through the air and water supply systems when the endoscope device is being used.

There have been therefore developed two kinds of endoscope devices each having pumps capable of smoothly supplying air and water through the air and water supply pipe systems while pressure-supplying air into the nozzle to prevent the matters such as viscous liquid and blood from entering into it and also capable of sucking the air through a sucking opening to prevent excessive air from being supplied into the body cavity. One of them is of the type wherein pressure-supply and suction of air flowing through the air and water supply pipe systems are carried out by different pumps, each of which has its own drive source, to prevent the pipe systems from being jammed by the matters such as viscous liquid and blood, and the endoscope device of this type is disclosed in the Japanese Patent Disclosure No. 61-73634. The other one is of the duplex pump type wherein different pumps for carrying out the pressure-supply and suction of air are driven by a single drive means, and the endoscope device of this duplex pump type is disclosed in the Japanese Patent Disclosure No. 61-141340.

In the case where the pressure-supply and suction of air are to be carried out, it is needed that the amount of air supplied under pressure is set equal to that of air sucked to keep the pressure in the body cavity certain, that is, to prevent excessive air from being supplied into the body cavity.

In the case of the first type endoscope device wherein the pressure-supply and suction of air are conducted by different pumps, however, it is difficult to keep the amount of air supplied under pressure balanced relative to that of air sucked and even if the amount of air supplied under pressure exceeds quite a little that of air sucked, air supplied into the body cavity will become excessive when the endoscope device is used for a long time. In the case of the second type endoscope device, the amount of air supplied under pressure is balanced with that of air sucked by their own capacities of pumps. Therefore, any changes of the state in the endoscope device which have nothing to do with the pump capacities and which are seen, for example, when the amount of air sucked is decreased, that is, the effective sectional areas of the sucking passages is reduced when any one of a plurality of medical tools is inserted deeper and deeper into the sucking pipe system, cannot be overcome. In other words, the amount of air supplied under pressure is kept certain at all times even when the amount of air sucked is decreased as described above. This causes excessive air to be supplied into the body cavity.

SUMMARY OF THE INVENTION

The object of the present invention is therefore to prevent the supply of air and water from being made not smooth by matters such as viscous liquid and blood in the body cavity adhering to the nozzle in the front portion of the endoscope and to keep the pressure in the body cavity certain at all times by sucking the same amount of air as that of air supplied into the body cavity by the endoscope device.

This object of the present invention can be achieved by an endoscope device comprising an endoscope having a front end portion provided with a nozzle and a sucking opening, a means having a first passage connected to the nozzle to supply fluid to it, a suction means having a second passage connected to the sucking opening, and a means having a third passage connected to the first and second passages and serving to circulate the fluid in such a way that it is sucked through the sucking opening and jetted through the nozzle.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5 is a time chart showing operation timings of switches and valves shown in FIG. 4;

FIG. 6 is a view showing a pipe system of the endoscope device according to a variation of the second embodiment of the present invention;

FIG. 7 is a sectional view showing a suction change-over means in FIG. 6;

FIG. 10 is a front view showing the front end face of the endoscope device according to the third embodiment of the present invention;

FIG. 11 shows a pipe system of the endoscope device according to a variation of the third embodiment of the present invention;

FIG. 14 is a time chart showing the relation between detected pressures of a pressure sensor and the operation of an electromagnetic changeover valve in FIG. 13;

DETAILED DESCRIPTION OF THE PREFERRED EMBODIMENTS

Figure 1:
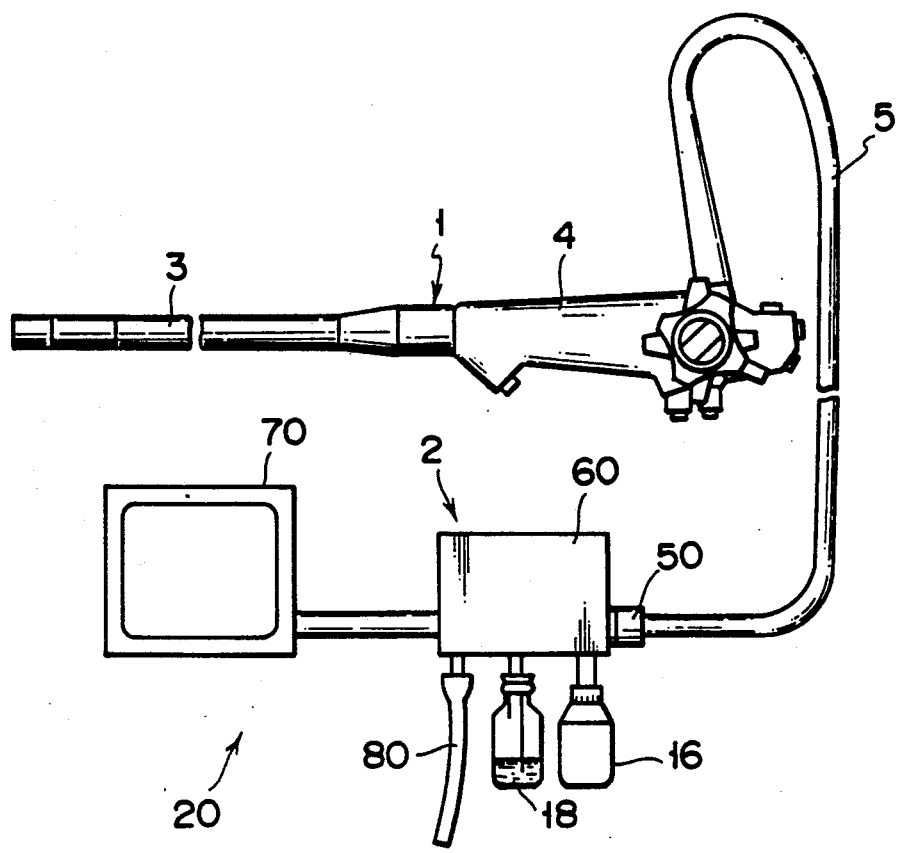
FIG. 1 is a side view showing the whole of an endoscope device according to the present invention.

As shown in FIG. 1, an endoscope device 20 according to the present invention includes an electronic endoscope 1. An elongated inserting section 3 which includes front and curved portions extends forward from an operating section 4 which serves as the grip of the electronic endoscope 1, and a universal code 5 is connected to a side of this operating section 4. The front end of this universal code 5 is connected to a video processor 60, in which a light source means is housed, through a connector 50. The video processor 60 has a signal processing circuit for processing image signals applied from the electronic endoscope 1 to display images on a monitor 70 connected to the video processor 60. The video processor 60 also houses an air and water supply pump 37, and a water supply tank 16 communicated with the air and water supply pump 37 through a pipe system, a circulating suction vessel 18, and a sucking tube 80 communicated with a suction pump 39 to form a sucking passage 13 are attached to the video processor 60.

It should be understood that the present invention is not limited to the electronic endoscope but can be applied to those of the optical fiber type.

Figure 2:
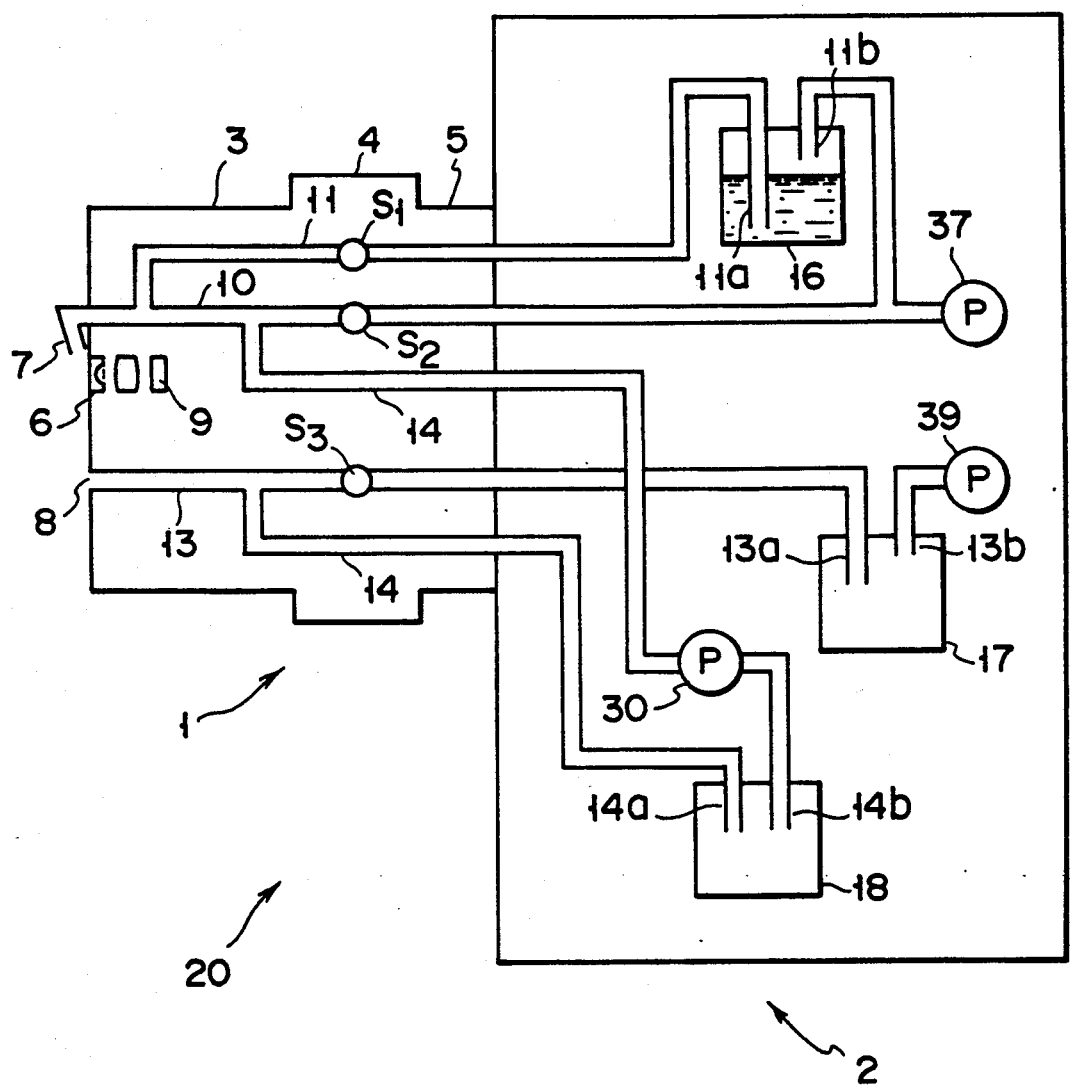
FIG. 2 is a view showing a pipe system of the endoscope device according to a first embodiment of the present invention.

FIG. 2 shows the inside of an endoscope device 20 which is a first embodiment of the present invention. A viewing window 6, a nozzle 7 and a suction opening 8 are arranged at the front end face of the inserting section 3 of the endoscope device 20. A solid pickup element 9 is located inside the viewing window 6 to photoelectrically convert images viewed through the viewing window 6 into image signals, which are sent to the video processor 60 in a control section 2. The nozzle 7 is opened, facing the outer surface of the viewing window 6, to jet cleaning water and air onto the outer surface of it. A gas supply passage 10 of the gas supply pipe system extending from the endoscope 1 to the control section 2 in the endoscope device 20 is connected to the nozzle 7.

A water supply passage 11 of the water supply pipe system arranged in the endoscope device 20 is connected to the gas supply passage 10 on the end thereof, extending from the endoscope 1 to the control section 2. A sucking passage 13 of the suction pipe system is connected to the suction opening 8, extending from the endoscope 1 to the control section 2 in the endoscope device 20. Further, a circulating passage of the circulating pipe system is arranged in the endoscope device 20 extending to communicate the gas supply passage 10 with the sucking passage 13.

The control section 2 includes the gas and water supply, suction and circulating pumps 37, 39 and 30 and the gas supply passage 10 extending from the endoscope 1 to the control section 2 is connected to the gas supply pump 37 while the water supply passage 11 branched and extended from the gas supply passage 10 is connected to the same pump 37 through the water supply tank 16.

The sucking passage 13 extending from the endoscope 1 is connected to the suction pump 39 through a sucking vessel 17. A portion of the circulating passage 14 which extends from the sucking passage 13 in the endoscope 1 is connected to the sucking side of the circulating pump 30 through the circulating vessel 18 in the control section 2 and another portion thereof which extends from the discharge side of the circulating pump 30 is connected to the gas supply passage 10 in the endoscope 1.

Figure 3:
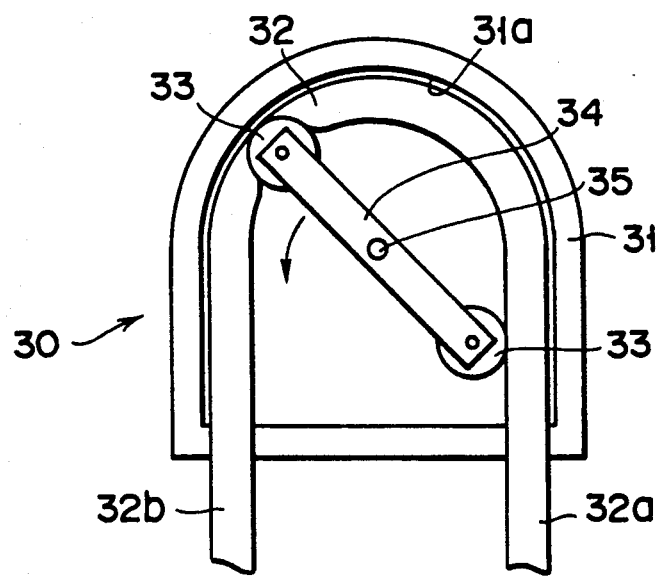
FIG. 3 schematically shows a circulating pump employed by the endoscope device in FIG. 2.

As shown in FIG. 3, the circulating pump 30 includes a case 31 whose top is shaped semicircular, and a fluid passage pipe 32 arranged along an inner face 31a of the case 31 and made of elastically deformable soft material. Sucking and discharging sides 32a and 32b of the fluid passage pipe 32 are connected to the circulating passage 14, respectively. A rotary stay 34 having a roller 33 at each of its both ends is arranged in the case 31 to rotate anticlockwise round a shaft 35, as shown by an arrow in FIG. 3. The rotary stay 34 is set to have such a length that allows its one roller 33 to press the fluid passage pipe 32 against the inner face 31a of the case 31 when this roller 33 reaches the semicircular portion of the case 31. When the rotary stay 34 is rotated, therefore, its one roller 33 moves on the fluid passage pipe 32 while pressing this soft pipe 32 against the inner face 31a of the case 31. As this roller 33 moves in this manner, gas in the fluid passage pipe 32 is continuously moved from the sucking side 32a of the pipe 32 to the discharging side 32b thereof.

As shown in FIG. 2, first, second and third valves $S_1$, $S_2$ and $S_3$ are arranged on the water and gas passages 11 and 10 and the sucking passage 13 to control the supply of cleaning water and air and the suction of them. The first and second valves $S_1$ and $S_2$ function to open one of them while the other is closed and to close both of them. The third valve $S_3$ functions only to open and close it. A connection end 11a of the water supply passage 11 connected to the water supply tank 16 is opened adjacent to the bottom of the tank 16 and kept in cleaning water in the tank 16. An opening 11b communicated with the air supply pump 37 to take pressurizing air into the tank 16 is located in the upper space in the water supply tank 16. The top surface of cleaning water in the tank 16 is pressurized by air pressure taken into the tank 16 through the opening 11b to thereby cause the cleaning water to be supplied to the water supply passage 11 through the open connection end 11a of the passage 11. An open connection end 13a of the suction passage 13 connected to the sucking vessel 17 is located nearer the bottom of the vessel 17 than a suction opening 13b connected to the vessel 17, and it is separated from this suction opening 13b. Materials such as viscous liquid and blood sucked through the suction opening 8 are thus caused to drop onto the bottom of the vessel 17 without being sucked into the suction opening 13b.

When the circulating pump 30 is kept operative at all times or made operative while using the endoscope 1, gas or air pressurized into the cavity of a human body is sucked into the suction opening 8 and guided into the circulating vessel 18 through the sucking passage 13 and the circulating passage 14 in this order. The circulating vessel 18 is closed while being communicated with the suction opening 8 and the circulating pump 30 through open ends 14a and 14b of the circulating passage 14. The same amount of air as that of air entered into the circulating vessel 18 can be thus supplied to the circulating pump 30. The air supplied to the circulating pump 30 is forced into the circulating passage 14 and the gas supply passage 10 and jetted onto the viewing window 6 through the nozzle 7 and then into the cavity of the human body.

Even when materials such as viscous liquid and blood except air are sucked through the suction opening 8, these materials are not sucked into the circulating pump 30 but collected in the circulating vessel 18 to supply only air under pressure. Air is jetted through the nozzle 7 at all times, thereby preventing viscous liquid and blood from entering into the endoscope 1 through the nozzle 7.

A second embodiment of the present invention will be described referring to FIGS. 4 and 5.

Figure 4:
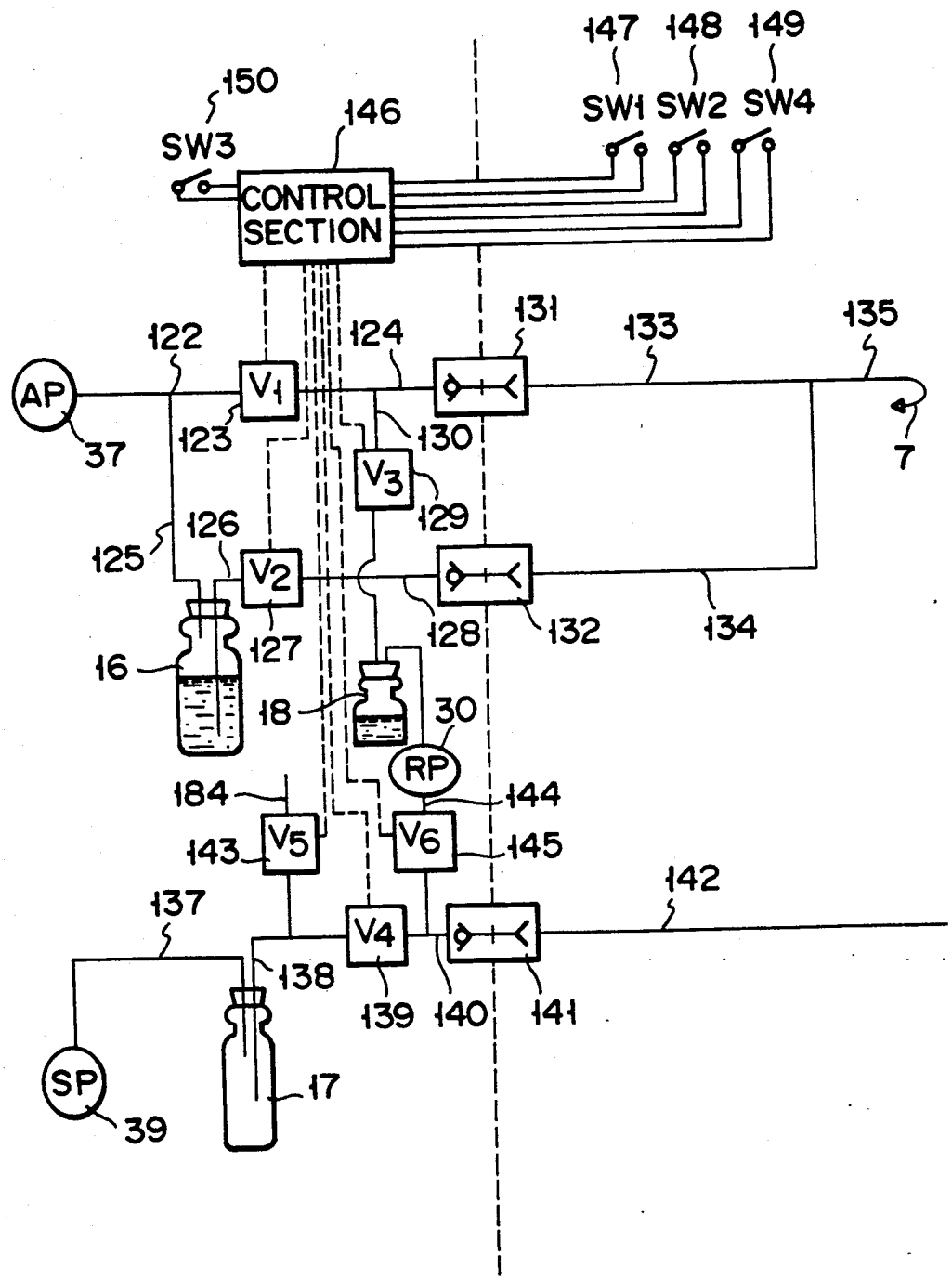
FIG. 4 shows a pipe system of the endoscope device according to a second embodiment of the present invention.

In the case of a pipe system shown in FIG. 4. a first air supply passage 122 is connected to the air and water supply pump 37 and it has a first electromagnetic valve (V1) 123 to which a second air supply passage 124 is connected. An air supply passage 125 is branched from the air supply passage 122 on the way thereof and communicated with and connected to the water supply tank 16. A first water supply passage 126 is connected to the water supply tank 16 and a second water supply passage 128 is connected to the first water supply passage 126 via a second electromagnetic valve (V2) 127. An air supply passage 130 is branched from the second air supply passage 124 and connected to the sucking bottle 18 through a third electromagnetic valve (V3) 129. Couplings or connectors 131 and 132 are attached to ends of the second air and water supply passages 124 and 128 and they are connected to air and water supply passages 133 and 134 located on the side of the endoscope 1. They are further combined with each other at the front end of the inserting section 3 to form an air and water supply passage 135, which is communicated with the nozzle 7 which is opened at the front end face of the endoscope inserting section 3, facing the viewing window.

A first sucking passage 137 is connected to the suction pump 39 at one end thereof and to the sucking bottle 17 at the other end thereof. Further, a second sucking passage 138 is connected to the sucking bottle 17. In addition, a third sucking passage 140 is connected to the second sucking passage 138 through a fourth electromagnetic valve (V4) 139. A coupling 141 is attached to another end of the third sucking passage 140 and it is connected to a sucking passage 142 located on the side of the endoscope 1. A leaking passage 184 is branched from the second sucking passage 138 and communicated with atmospheric air via a fifth electromagnetic valve (V5) 143.

A sucking circulation passage 144 is branched from the third sucking passage 140 and it is connected to a sixth electromagnetic valve (V6) 145 and the circulating pump 30 and then to the sucking vessel 18 on the discharge side of the pump 30. The first to sixth electromagnetic valves 123, 127, 129, 139, 143 and 145 are electrically connected to a control section 146, to which switches (SW1) 147, (SW2) 148 and (SW4) 149 arranged at the operation section 4 of the endoscope 1 and a switch (SW3) 150 arranged on a video processor 116 are connected.

In the case of the endoscope device arranged as described above, air and water supplies are usually made during organ examination conducted by the endoscope device by turning on and off the switches 147 and 148 arranged at the operation section 4, as shown in FIG. 5. When the switch 147 is turned on, the first electromagnetic valve 123 is opened by the control section 146 to supply air through the air passage 133. When the switch 148 is turned on, the control section 146 similarly opens the second electromagnetic valve 127 to supply cleaning or washing water into the water supply passage 134.

The suction is carried out by turning on and off the switch 149 arranged at the operation section 4. When the switch 149 is put on, the fifth electromagnetic valve 143 is closed and the fourth one 139 is opened by the control section 146 responsive to the switch 149 turned on, although only the fifth electromagnetic valve 143 is usually kept open and waiting. The suction is thus carried out.

The circulation is carried out as follows. When the changeover switch (SW3) 150 for starting and stopping the circulation is turned on, the sixth and third electromagnetic valves 145 and 129 are opened and the pump 30 is thus made operative to suck liquids in the cavity of the human body into the sucking vessel 18 through the sucking passages 142, 140 and 144. The liquids thus sucked into the sucking vessel 18 are separated from air and only the air thus separated is supplied, same in amount as air sucked, onto the viewing window through the nozzle 7 via the passages 130, 124, 133 and 135. The circulation is stopped by turning off the switch 150. because the pump 30 is stopped and both of the third and sixth electromagnetic valves 129 and 145 are closed.

According to the second embodiment of the present invention, the sucking vessel 18 is located downstream the pump 30 or on the discharge side of the pump 30 which serves as the circulating means. This prevents any of the sucking passages from being jammed and air in the sucking bottle from being sent (or forced) into the cavity of the human body when the forceps or the like is inserted into the sucking passages, thereby enabling the amount of air supplied to be made equal to that of air sucked.

FIGS. 6 and 7 show a variation of the second embodiment according to the present invention, which is related to a means for mechanically changing over the modes of supplying and sucking air and water.

In FIG. 6, reference numeral 151 represents an air supply pump housed in the light source means. This air supply pump 151 is communicated with a first air supply passage 152 in the universal code 5 and also with an air/water changeover means 153 at the operation section 4. A passage 154 is branched from the fist air supply passage 152 and communicated with a water supply tank 155 to pressurize water in the tank 155. A first water supply passage 156 is connected to the water supply tank 155 and communicated with the air/water changeover means 153. Further, second air and water supply passages 157 and 158 in the inserting section 3 of the endoscope 1 are connected to the air/water changeover means 153 and opened at their front ends through air and water supply nozzles 159 and 160.

On the other hand, the suction pipe system is formed as follows. A first sucking passage 162 is connected to a suction pump 161, communicated with a second sucking passage 164 in the universal cord 5 of the endoscope 1 through a sucking bottle 163 and then with a suction changeover means 165 at the operation section 4. A third sucking passage 166 in the inserting section 3 is communicated with the suction changeover means 165 and opened there at the front end thereof.

A first circulation-sucking passag 167 is branched from the third sucking passage 166 and communicated with a pump 168 which serves as the circulating means. A circulation-sucking bottle 170 is communicated with the discharge side of the pump 168 through a circulation-air supplying passage 169. A first circulation-air supplying passage 171 is connected to the circulation-sucking bottle 170 and combined with the second air supply passage 157. The pump 168 is electrically connected to a control section 172. Further, a switch (SW10) 173 arranged on the video processor 60 is connected to the control section 172.

The suction changeover means 165 is arranged as shown in FIG. 7. Reference numeral 174 represents a part of the operation section 4, which is fixed by screwing a nut 176 onto a suction cylinder 175. The second and third sucking passages 164 and 166 are connected to the cylinder 175. An attachment 177 made of elastic material is freely detachably attached to the nut 176. Further, the attachment 177 is provided with a guide member 180 which defines the slide of a piston 179 screwed into a button 178. The piston 179 is provided with a stopper 182 which prevents the piston 179 from coming out of the guide member 180 because of a spring 181 arranged between the button 178 and the guide member 180. The piston 179 has a communication opening 183 located higher than the stopper 182.

The suction of air and water supplied is carried out as follows by the suction changeover means. Air supply is carried out in such a way that air supplied from the air supply pump is jetted through the air supply nozzle 159 by closing a leak hole (not shown) of the air/water changeover means 153. Water supply is carried out in such a way that when the air/water changeover means 153 is pushed by one step, cleaning water in the water supply tank 155 is pressurized by air supplied from the air supply pump 151 and jetted through the water supply nozzle 160. Suction is conducted in such a way that when the button 178 is pushed, the second and third sucking passages 164 and 166 are communicated with each other by the communication opening 183 to allow the suction pump 161 to suck air and water supplied.

On the other hand, circulation is carried out as follows. When the switch 173 is turned on, the control section detects it to make the circulation pump 168 operative. The pump 168 made thus operative sucks fluid which is present around the front end of the inserting section 3 of the endoscope 1 through the third sucking passage 166 and the circulation-sucking passage 167 and the fluid thus sucked is forced into the circulation-sucking vessel 170 through the first circulation-air supply passage 169. The fluid is then separated from air here in the vessel 170 and only air thus separated is forced into the second circulation-air supply passage 171 and jetted through the air supply nozzle 159 via the second air supply passage 157. The circulation-sucking vessel 170 is located in this case on the discharge side of (or downstream) the pump 168 which serves as the circulation means. This prevents the third sucking passage 171 from being jammed and air in the circulation-sucking vessel 170 from being forced out of the vessel 170 when the examination forceps is inserted into the sucking passages. Therefore, the amount of air supplied cannot exceed that of air sucked. In short, the amount of air supplied cannot become excessive. The cap of the circulation-sucking bottle is screwed onto or into the bottle or stopped by a stopper not to come out of the bottle because of pressure applied from the pump.

Figure 8:
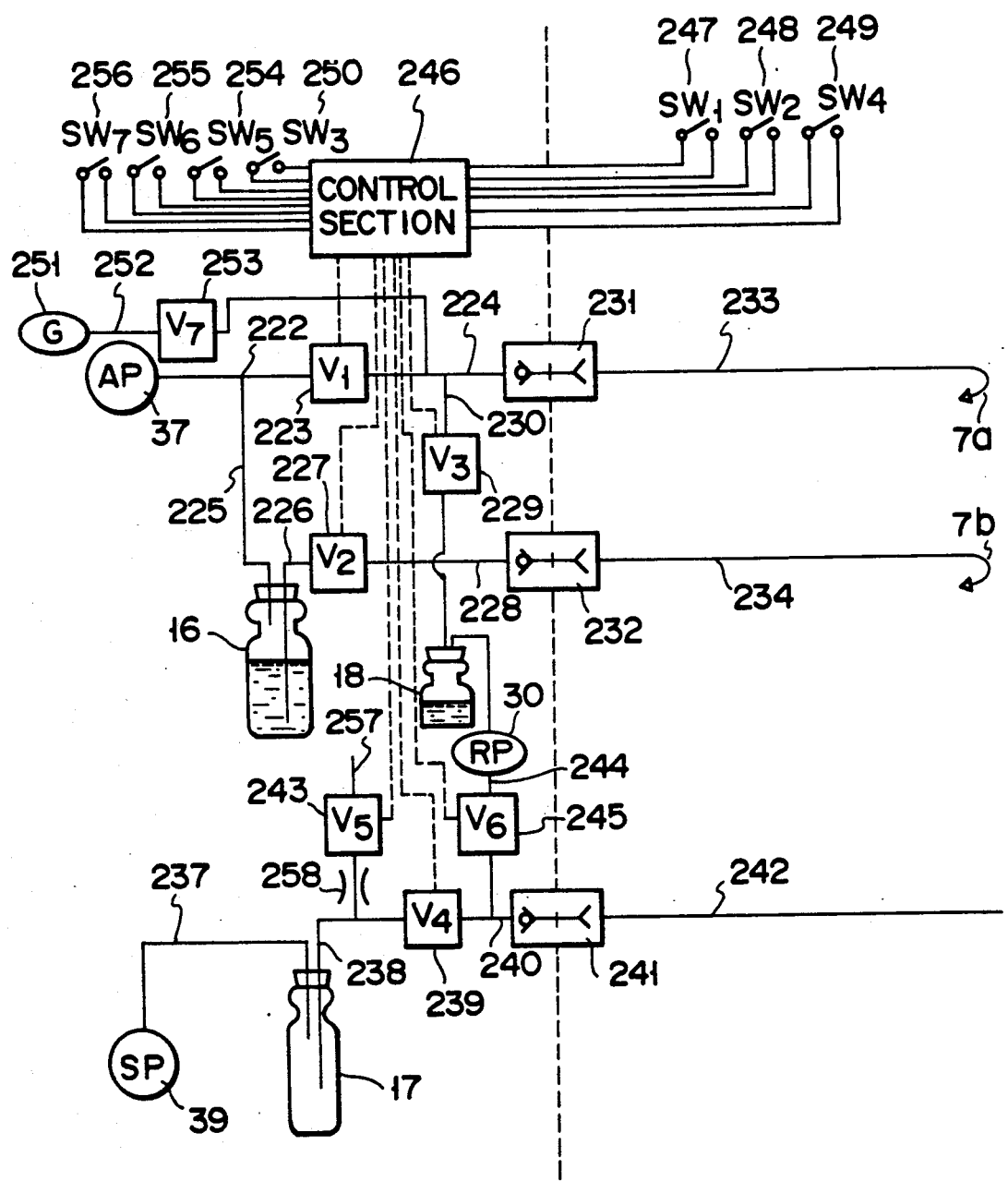
FIG. 8 shows a pipe system of the endoscope device according to a third embodiment of the present invention.
Figure 9:
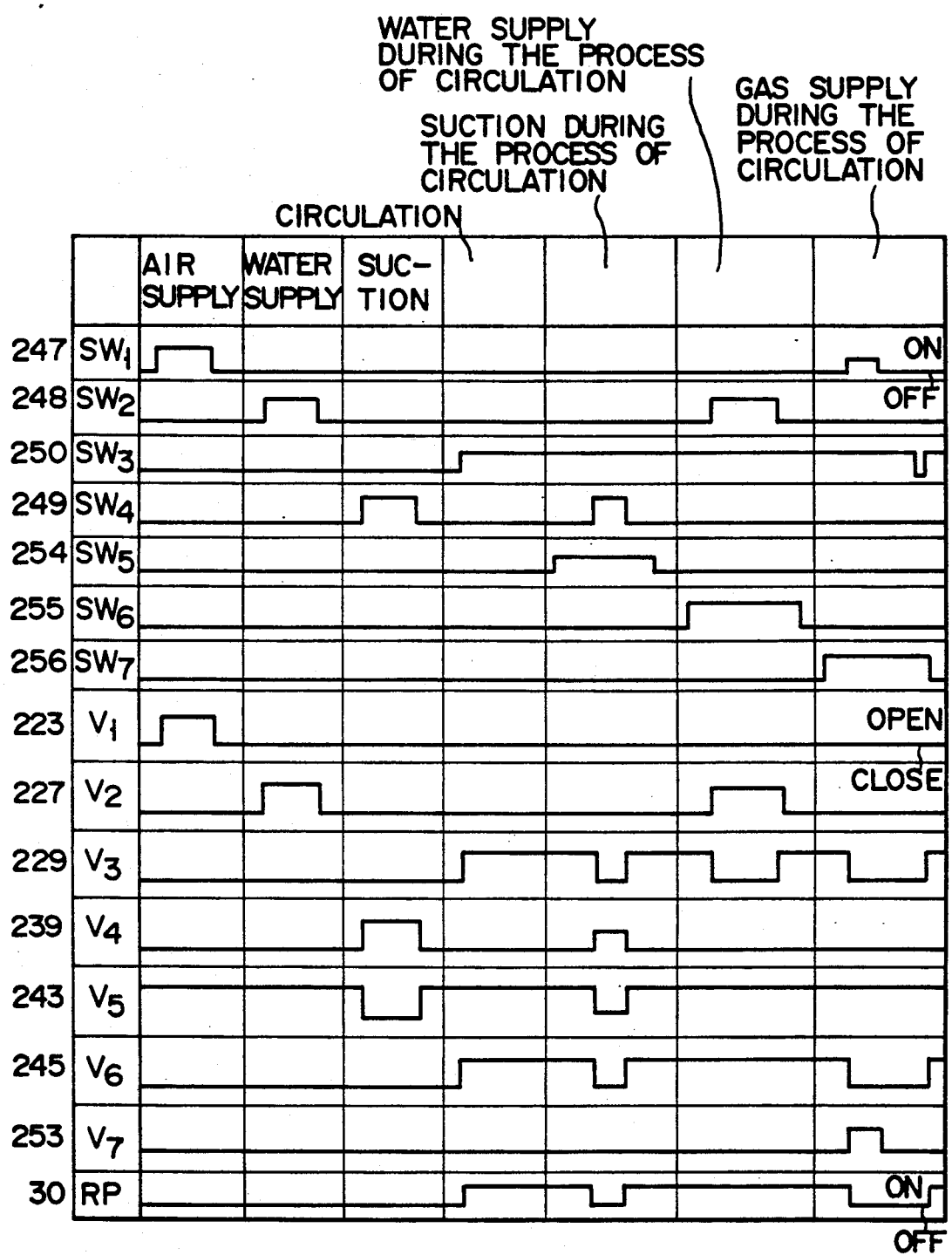
FIG. 9 is a time chart showing operation timings of switches and valves in FIG. 8.

FIGS. 8 through 10 show a third embodiment of the present invention.

In the case of a pipe system shown in FIG. 8, a first air supply passage 222 is connected to an air supply pump 37 and it includes a first electromagnetic valve (V1) 223 at another end thereof. A second air supply passage 224 is connected to this first electromagnetic valve 223. An air supply passage 225 which serves to supply water is branched from the air supply passage 22 on the way thereof and communicated with a water supply tank 16. A first water supply passage 226 is connected to the water supply tank 16 and communicated with a second water supply passage 228 via a second electromagnetic valve (V2) 227. A circulationair supply passage 230 is branched from the second air supply passage 224 and communicated with the circulation-sucking vessel 18 through a third electromagnetic valve (V3) 229. Check valves 231 and 232 are attached to the other ends of the second air and water supply passages 224 and 228 and connected to air and water supply passages 233 and 234 located on the side of the endoscope 1. These air and water supply passages 233 and 234 are communicated with nozzles 7a and 7b which are opened at the front end of the endoscope 1, facing the viewing window.

Reference numeral 251 represents a ga tank in which non-combustible gas is stored and to which a first gas passage 252 is connected. The first gas passage 252 is also connected to the second air supply passage 224 through a seventh electromagnetic valve (V7) 253. On the other hand, a first sucking passage 237 is connected to the suction pump 39 and the sucking bottle 17. A second sucking passage 238 is connected to the sucking bottle 17 and a third sucking passage 240 is connected to the second sucking passage 238 via a fourth electromagnetic valve (V4) 239. A check valve 241 is attached to the other end of the third sucking passage 240 and connected to a sucking passage 242 located on the side of endoscope 1. A leaking passage 257 is branched from the second sucking passage 238 and communicated with atmospheric air through a fifth electromagnetic valve (V5) 243. The leaking passage 257 is provided with an orifice 258, which serves to keep the pump 39, the first sucking passage 237, the bottle 17 and the second sucking passage 238 negative in pressure even at the time of leakage.

A circulation-sucking passage 244 is branched from the third sucking passage 240 and connected to the circulation-sucking vessel 18 via a sixth electromagnetic valve (V6) 245 and the circulating pump 30. The first-seventh electromagnetic valves 223, 227, 229, 239, 243, 245 and 253 are electrically connected to a control section 246. Further, switches (SW1) 247, (SW2) 248, (SW4) 249 arranged at the operation section 4 of the endoscope 1 and switches (SW3) 250, (SW5) 254, (SW6) 255, (SW7) 256 arranged on the video processor 60 are also connected to the control section 246.

In the case of the above-described endoscope device, air and water supplies during the body cavity examination conducted by the endoscope device are carried out by turning on and off the switches 247 and 248 arranged at the operation section 4, as seen in a time chart in FIG. 9. When the switch 247 is turned on, the first electromagnetic valve 223 is opened by the control section 246 to thereby supply air through the air supply passage 233. When the switch 248 is put on, the control section 246 similarly open the second electromagnetic valve 227 to thereby send cleaning water into the water supply passage 234.

Suction is carried out by turning on and off the switch 249 arranged at the operation section 4. When the switch 249 is turned on, the fifth electromagnetic valve 243 is closed and the fourth electromagnetic valve 239 is opened by the control section 246 in response to the switch 249 turned on although only the fifth electromagnetic valve 243 is usually kept open and waiting. The suction is thus carried out.

Circulation is carried out as follows. When the changeover switch (SW3) 250 which serves to start and stop the circulation is turned on, the sixth and third electromagnetic valves 245 and 229 are made open and the circulation pump 30 is made operative to suck liquid in the body cavity into the circulation-sucking bottle 18 through the sucking passage 242, the third sucking passage 240 and the circulation-sucking passage 244. The liquid sucked into the vessel 18 is separated into liquid matters such as viscous liquid and air and only the air is supplied, same in amount as air sucked, from the nozzle 7a through the circulation-air supply passage 230, the second air supply passage 224 and the air supply passage 233. When the switch 250 is turned off, the circulation pump 30 is stopped and the third and sixth electromagnetic valves 229 and 245 are closed. The circulation is thus stopped.

The air and water supplies and suctions conducted during the process of circulation will be described.

In the case where the suction is to be carried out during the process of circulation, the switch (SW5) 254 which serves to control the circulation to be stopped and continued during the process of suction is turned on and the suction switch (SW4) 249 is also turned on under such a state that the switch (SW3) 250 which serves to stop and continue the circulation is turned on, that is, the suction pump 39 is under operation while keeping the sixth and third electromagnetic valves 245 and 229 open. The fifth electromagnetic valve 243 is thus closed and the fourth one is opened to thereby start the suction, while the third and sixth electromagnetic valves 229 and 245 are closed and the pump is stopped at the same time. When the switch (SW4) 249 is turned off, the fifth electromagnetic valve 243 is opened and the fourth one 239 is closed to thereby stop the suction while the third and sixth electromagnetic valves 229 and 245 are opened and the pump 30 is made operative to thereby start the circulation.

Description will be made on the water supply during the process of circulation. When water is supplied during the process of air circulation in the case of the endoscope which has the air and water supply nozzles 7a and 7b, water supplied through the water supply nozzle 7b is blown away, as shown in FIG. 10, by air which is kept jetted through the air supply nozzle 7a, so that the surface of a lens in the observation window 6 cannot be washed clean. This makes it necessary to use a means for closing the circulation-air supply passages only while water is being supplied. In order to stop the circulation during the process of water supply, the switch (SW6) 255 which serves to stop the circulationair supply during the process of water supply is turned on and the switch (SW2) 248 is turned on under such a state that the switch 250 is turned on, that is, the third and sixth electromagnetic valves 229 and 245 are opened while the pump 30 is being operated. The second electromagnetic valves 227 is thus opened to start the water supply and the third electromagnetic valve 229 is closed to stop the circulation-air supply at the same time. When the switch 248 is turned off, the second electromagnetic valve 227 is closed while the third one 229 is opened and the water supply is thus stopped while the circulation-air supply is again started. This enables the viewing window 6 to be surely washed clean even when the water supply is carried out during the process of circulation.

Description will be made on the gas supply during the process of circulation. When the seat of a disease in the cavity of the human body is to be cut off or treated by a high-frequency surgical knife, for example, during the cavity examination conducted by the endoscope device, non-combustible gas is supplied to prevent explosion. When the circulation is still carried out even after the gas supply, however, the gas is diluted with air in the vessel 18 and passages. When the amount of gas supplied is small, therefore, the possibility of explosion is left. When the density of gas is made so sufficient as to solve this problem, the time needed becomes substantially long. This embodiment of the present invention solves this problem by controlling the circulation to be automatically stopped when the gas supply is started. When the gas supply is to be carried out during the process of circulation, the air/gas changeover switch (SW7) 256 is turned on and the switch 247 which serves to supply air is also turned on. The seventh electromagnetic valve 253 is thus opened to supply gas, while the third and sixth electromagnetic valves 229 and 245 are closed and the circulation pump 30 is stopped. When the switch 247 is turned off, only the seventh electromagnetic valve 253 is closed and kept closed. When the circulation is to be again started, the circulation switch 250 is again turned on.

When control is conducted in this manner, the gas supplied cannot be diluted with air and safety can be guaranteed.

Figure 12:
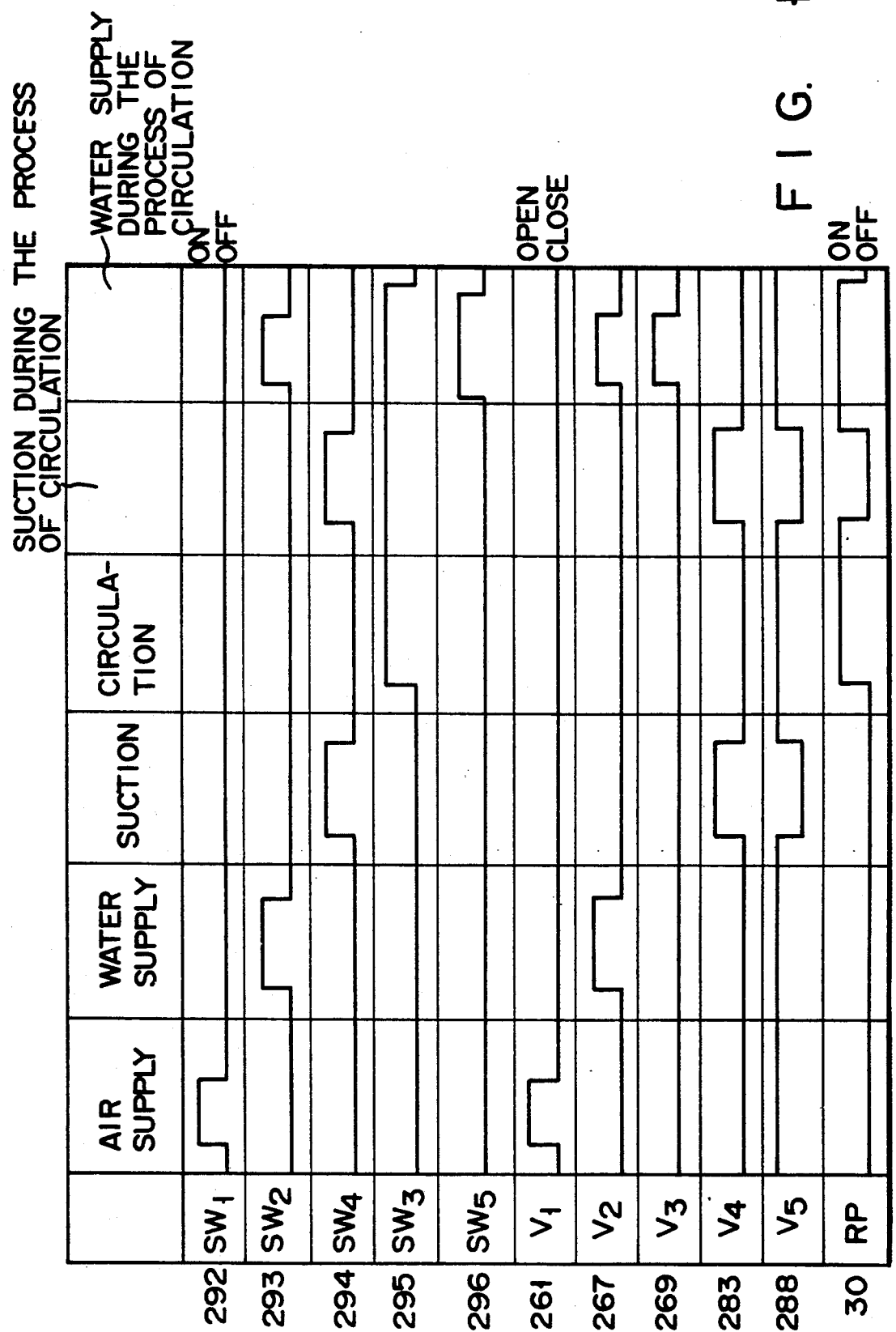
FIG. 12 is a timing chart showing operation timings of switches and valves in FIG. 11.

FIGS. 11 and 12 show a variation of the third embodiment according to the present invention.

In the case of a pipe system shown in FIG. 11, a first air supply passage 260 is connected to an air supply pump 259 and it includes at the other end thereof a first electromagnetic valve (V1) 261 to which a second air supply passage 263 is connected. An air supply passage 264 for water supply is branched from the air supply passage 260 on the way thereof and communicated with a water supply tank 265, to which a first water supply passage 266 is connected and a second water supply passage 268 is also connected via a second electromagnetic valve (V2) 267. A circulation-air supply passage 270 is branched from the second air supply passage 263 and communicated with a circulation sucking vessel 18 through a third electromagnetic valve (V3) 269 which is a three ports valve. A by-pass passage 272 which is communicated with the second water supply passage 268 is connected to another outlet of the third electromagnetic valve (V3) 269. Couplings 273 and 274 are attached to the other ends of the second air and water supply passages 263 and 268 and connected to air and water supply passages 275 and 276 located on the side of the endoscope 1. The air and water supply passages 275 and 276 are communicated with nozzles 277 and 278 which are opened at the front end of the endoscope 1, facing the viewing window 6. On the other hand, a first sucking passage is connected to a suction pump 279 and a sucking bottle 281. Further, a second sucking passage 282 is also connected to the sucking bottle 281. A third sucking passage 284 is connected to the second sucking passage 282 through a fourth electromagnetic valve (V4) 283. A coupling 285a is attached to the other end of the third sucking passage 284 and connected to a sucking passage 286 located on the side of the endoscope 1. A leaking passage 287 is branched from the second sucking passag 282 and communicated with atmospheric air through a fifth electromagnetic valve (V5) 288.

A circulation-sucking passage 285b is branched from the third sucking passag 284 and connected to a circulation-sucking vessel 289 via a circulation pump 30. The first to fifth electromagnetic valves 261. 267, 269, 283 and 288 are electrically connected to a control section 291. On the other hand, switches (SW1) 292, (SW2) 293, (SW4) 294 arranged at the operation section 4 of the endoscope 1 and switches (SW3) 295. (SW5) 296 arranged on the video processor 60 are also connected to the control section 291.

When the endoscope device has the pipe system arranged as described above, air and water supplies and suctions are carried out in the same manner as in the case of the third embodiment. Description on them will be omitted accordingly.

Since the outlet of the third electromagnetic valve 269 is usually changed over to communicate with the second air supply passage 263 as shown in FIG. 12, circulation is carried out by turning on the circulation switch 295 to make the circulation-air supply pump 271 and the circulation pump 30 operative.

When suction is to be carried out during the process of circulation, the suction switch 294 is turned on under the state that the circulation switch 295 is turned on. The fifth electromagnetic valve 288 is thus closed and the fourth one 283 is opened to thereby start the suction. At the same time, the circulation-air supplied and circulation pump 30 is stopped. When the suction switch 294 is turned off, the fourth electromagnetic valve 283 is closed and the fifth one 288 is opened, while the circulation pump 30 is made again operative.

When water supply is to be carried out during the process of circulation, the switch 293 is turned on under the state that the switch 296 which serves to change over the circulation-air supply from the air supply passage 275 to the water supply passage 276 during the process of water supply is turned on. The second electromagnetic valve 267 is thus opened to carry out water supply. At the same time, the outlet of the third electromagnetic valve 269 is changed over to the second water supply passage 268 to thereby supply air to the water supply passage 276. According to this control manner, water supplied during the process of circulation is spray-jetted sufficiently to wash the observation window cleaner.

Figure 13:
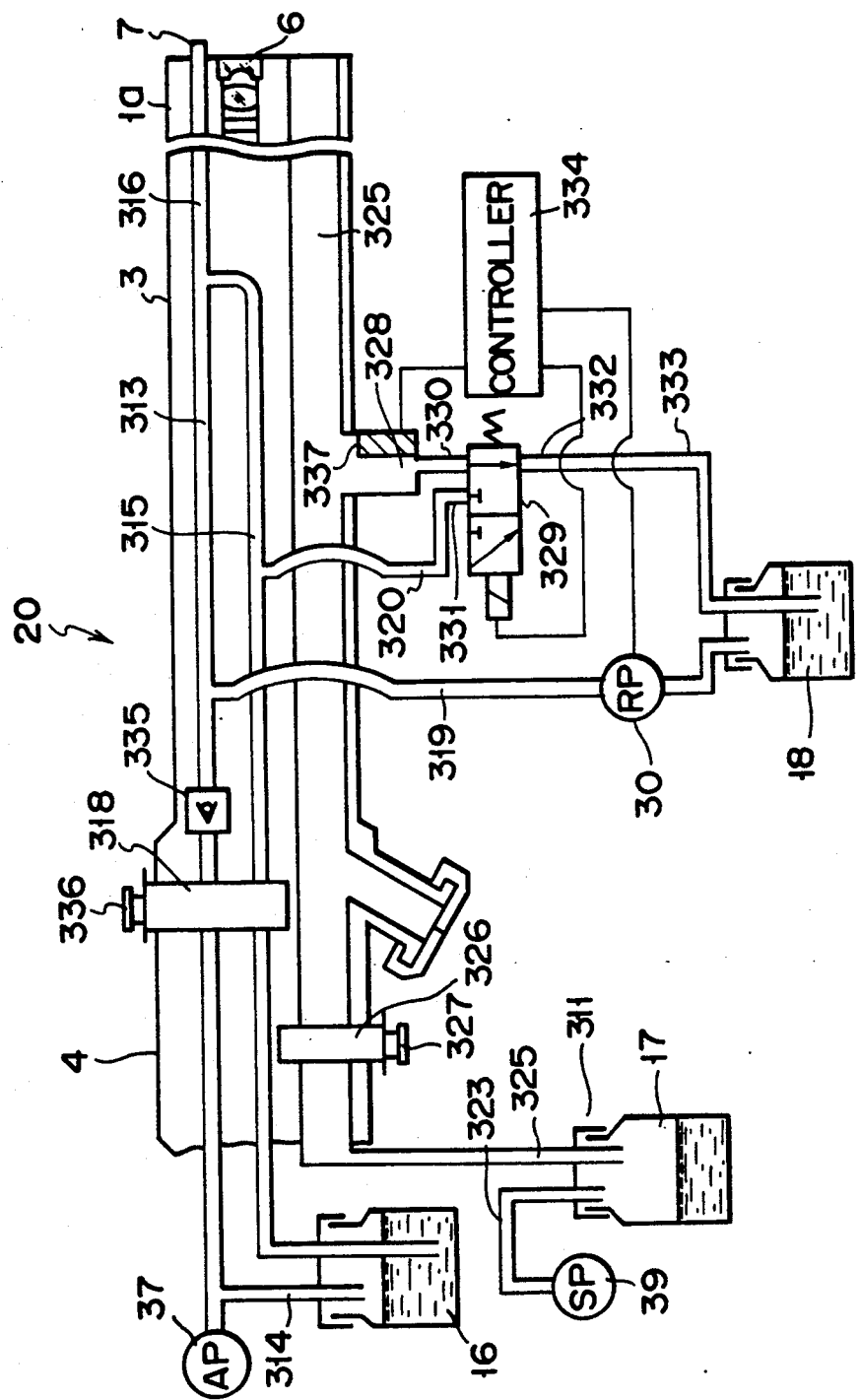
FIG. 13 shows a pipe system of the endoscope device according to a fourth embodiment of the present invention.

FIGS. 13 and 14 show a fourth embodiment of the present invention.

As shown in FIG. 13, an air supply passage 313 is connected to the air supply pump 37 of the endoscope device 20. An air supply passage 314 for water supply is branched from the air supply passage 313 on the way thereof and communicated with the water supply tank 16. A water supply passage 315 is also connected to the water supply tank 16. The air and water supply passages 313 and 315 pass through the universal cord 5, the operation section 4 and the inserting section 3, and they are combined with each other to form an air and water supply passage 316 in the front end portion of the inserting section 3. The air and water supply passage 316 is communicated with the nozzle 7 which is opened, facing the viewing window 6 at the front end 1a of the endoscope 1. The air and water supply passages 313 and 315 are connected to an air/water changeover valve 318 on their ways at the operation section 4. One ends of circulation-air supply and by-pass circulation passages 319 and 320 are connected to those points of the air and water supply passages 313 and 315 which are located nearer the inserting section 3 than the air/water changeover valve 318 is. The other end of the circulation-air supply passage 319 is connected to the circulation-sucking vessel 18 via the circulation roller pump 30, while the other end of the by-pass circulation passage 320 is connected to an electromagnetic changeover valve 329 which serves as a passage changeover means, as will be described later.

A first sucking passage 323 is connected to the suction pump 39 of a suction means 311 at one end thereof and to the sucking vessel 17 at the other end thereof. Further, a sucking passage 325 is connected to the sucking vessel 17. The sucking passage 325 is opened at the front end 1a of the endoscope 1, passing through the universal cord 5, the operation section 4 and the inserting section 3, and a suction changeover valve 326 is attached to the sucking passage 325 on the way thereof at the operation section 4.

The suction changeover valve 326 has a leaking path and when a button 327 is not pushed, the sucking passage 325 located on the side of the universal cord 5 is communicated with atmospheric air through the leaking path of the suction changeover valve 326. When the button 327 is pushed, the one portion of the sucking passage 325 which extends from the suction changeover valve 326 to the sucking vessel 17 is communicated with the other portion thereof which extends from the changeover valve 326 to the front end of the endoscope 1, so that matters such as viscous liquid and dirt in the body cavity can be sucked through the sucking passage 325 by the suction pump 39. A circulation-sucking passage 328 is branched from the portion of the sucking passage 325 which extends from the changeover valve 326 to the inserting section 3, and it is connected to the circulation-sucking vessel 18 via an electromagnetic changeover valve 329. The circulation-sucking passage 328 includes therein a pressure sensor 337 which detects pressure in the passage 328.

The electromagnetic changeover valve 329 is of the three-port type wherein a first port 330 is connected to the circulation-sucking passage 328, a second port 331 to the by-pass circulation passage 320 and a third port 332 to a connection passage 333.

The first port 331 is communicated with the third one 332 under normal state. The other end of the connection passage 333 is connected to the circulation sucking vessel 18. When pressure measured by the pressure sensor 337 becomes lower than the discharging pressure of the circulation pump 30, the circulation pump 30 and the electromagnetic changeover valve 329 are made operative by a control means 334. A check valve 335 is arranged on the air supply passage 313 between the air/water changeover valve 318 and that point of the passage 313 from which the circulation-air supply passage 319 is branched to prevent the matters such as viscous liquid and blood in the body cavity from flowing backward into the passage 313. The air/water changeover valve 318 has a leaking path and the air supply passage 313 located on the side of the universal cord 5 is communicated with atmospheric air through this leaking path under normal state. When the leaking path is closed by a button 336, the one portion of the 313 which extends from the changeover valve 318 to the air pump 37 is communicated with the other portion thereof which extends from the valve 318 to the front end of the endoscope 1 to thereby allow air to be supplied through the nozzle 7. Air curtain is thus formed in front of the observation window 6 by air supplied through the nozzle 7 to thereby guarantee a field of view through the observation window 6. When the button 336 is pushed, the one portion of the air supply passage 313 is shielded from the other portion thereof while the one portion of the water supply passage 315 is communicated with the other portion thereof. As the result, water pressurized by the pressure of the air pump 37 is supplied through the nozzle 7 via the water supply passage 315. Water is supplied to the front surface of the observation window 6 through the nozzle 7 to thereby guarantee the field of view through the observation window 6.

When the circulation pump 30 is made operative by control signal applied from the control means 334, fluid in the body cavity is sucked into the circulstion-sucking vessel 18 through the circulation-sucking passage 328, the passage in the electromagnetic valve 329 and the connection passage 333. Circulation is thus carried out between the air supply passage 313 and the sucking passage 325. The fluid sucked into the circulation-sucking vessel 18 is separated into liquid such as viscous liquid and air and only the air is supplied, same in amount as that of air sucked, through the nozzle 7, passing through the circulation-air supply passage 319, the air supply passage 313 and the air/water supply passage 316. When pressure measured by the pressure sensor 337 in the circulation sucking passage 328 becomes lower than that under steady state (or under the state that suction is not carried out through the sucking passage and that not treating tool is inserted into the sucking passage), as shown in FIG. 14, the control means 334 operates to make the rotation number of the circulation pump 30 smaller, so that the amount of air supplied through the nozzle 7 can be made smaller. When the pressure measured by the pressure sensor 337 becomes still lower, the control means 334 operates to change over the passage in the electromagnetic changeover valve 329. The second port 331 is thus communicated with the third one 332, thereby enabling a by-pass circulation passage to be formed by the by-pass circulation passage 320, the passage in the electromagnetic changeover valve 329, the connection passage 333, the circulation-sucking vessel 18 and the circulation-air supply passage 319, and circulation fluid is not jetted through the nozzle 7 but circulated in the endoscope device. When the pressure measured by the pressure sensor 337 becomes equal to that under steady state, the electromagnetic changeover valve 329 is again made operative to return the endoscope device to its original state.

Figure 15:
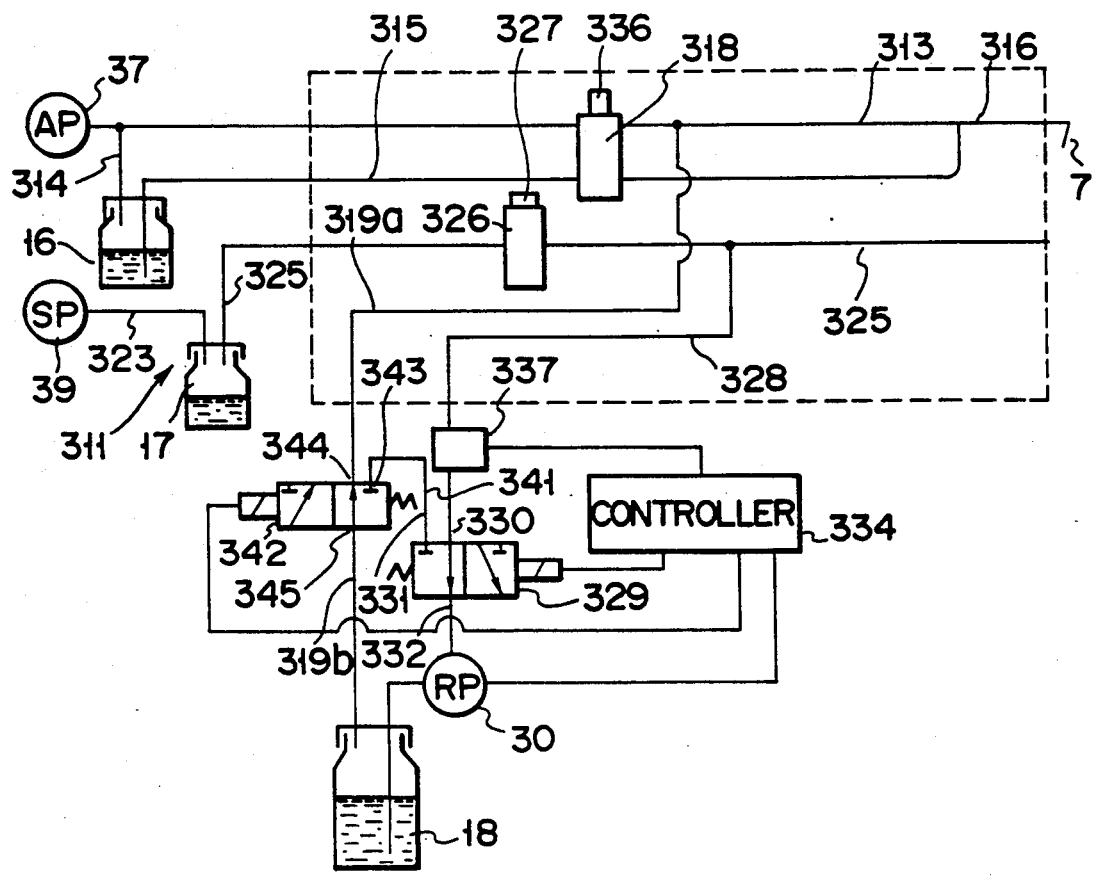
FIG. 15 is a view showing a pipe system of the endoscope device according to a first variation of the fourth embodiment of the present invention.
Figure 16:
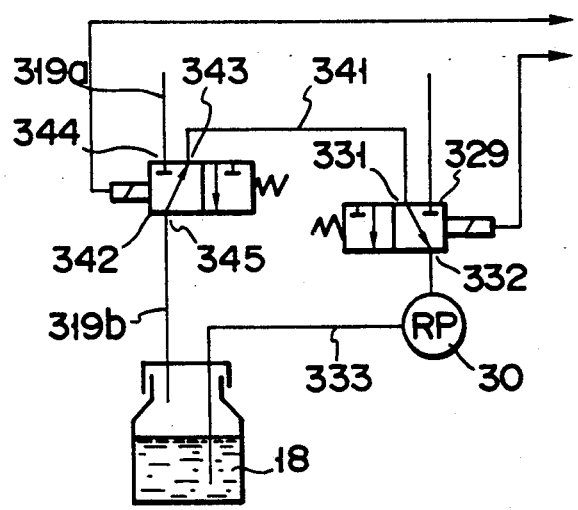
FIG. 16 shows the piping of an electromagnetic changeover valve in FIG. 15.

FIGS. 15 and 16 show a variation of the fourth embodiment according to the present invention.

When the by-pass circulation passage is formed in the case of the above-described fourth embodiment, water stayed in the water supply passage 315 between a point at which the water supply passage 315 is combined with the air supply passage 313 and another point at which by-pass circulation passage 320 is combined with the water supply passage 315 flows into the circulation-sucking vessel 18. When water supply is started next, therefore, the time during which the head of water supplied reaches the nozzle 7 becomes longer as compared with the case where water is kept stayed there in the water supply passage 315. In other words, the response of water supplied is delayed. The variation of the fourth embodiment is intended to solve this problem.

An electromagnetic changeover valve 342 is attached to the circulation-air supply passage 319 on the way thereof and a by-pass circulation passage 341 is arranged between the electromagnetic changeover valves 329 and 342 instead of the by-pass circulation passage 320. The variation is same in other arrangements as the fourth embodiment.

One end of the by-pass circulation passage 341 is connected to the second port 331 of the electromagnetic changeover valve 329 and the other end thereof to a first port 343 of the electromagnetic changeover valve 342. Circulation-air supply passages 319a and 319b are connected to second and third ports 344 and 345 and thus communicated with each other.

According to this variation of the fourth embodiment, the control means 334 operates to make the rotation number of the circulation pump 30 smaller when pressure measured by the pressure sensor 337 in the circulation-sucking passage 328 becomes lower than that under steady state. When the pressure measured by the pressure sensor 337 becomes still lower, the control means 334 further operates to make the electromagnetic changeover valves 329 and 342 operative at the same time so as to create such a state as shown in FIG. 16. In short, the second and third ports 331 and 332 of the electromagnetic changeover valve 329 are communicated with each other and the first and third ports 343 and 345 are communicated with each other. The by-pass circulation passage is thus formed by the circulation-air supply passage 319b, the electromagnetic changeover valve 342, the by-pass circulation passage 341, the electromagnetic changeover valve 329, the connection passage 333, the circulation pump 30 and the circulation-sucking vessel 18.

Therefore, the water supply passage 315 is not used as the by-pass circulation passage 341 and this enables the response of water supplied to be made faster.

As described above, the pressure sensor 337 is arranged in the circulation-sucking passage 328 to check the balance of the amount of fluid sucked by the circulation pump 30 relative to the amount of fluid discharged from the pump 30. This can prevent the body cavity from being excessively expanded by air excessively supplied. Even if a mucous membrane in the body cavity sticks to the distal end of the inserting section, no strong force is exerted on the membrane, and no troubles will occur. Further, the circulation passage can be instantly made usable even when the electromagnetic changeover valves are changed over, because the circulation pump 30 is under operation at all times.

Figure 17:
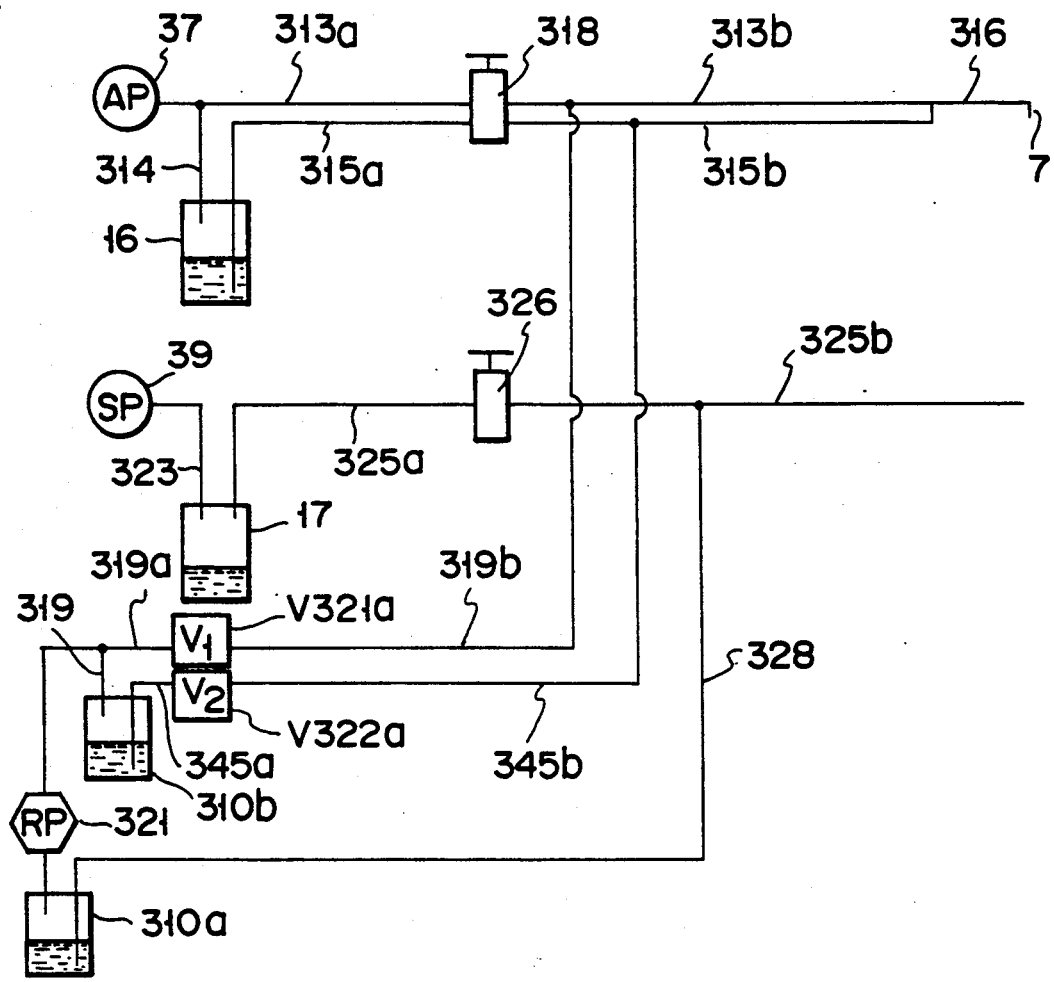
FIG. 17 shows a pipe system of the endoscope device according to a second variation of the fourth embodiment of the present invention.
Figure 18:
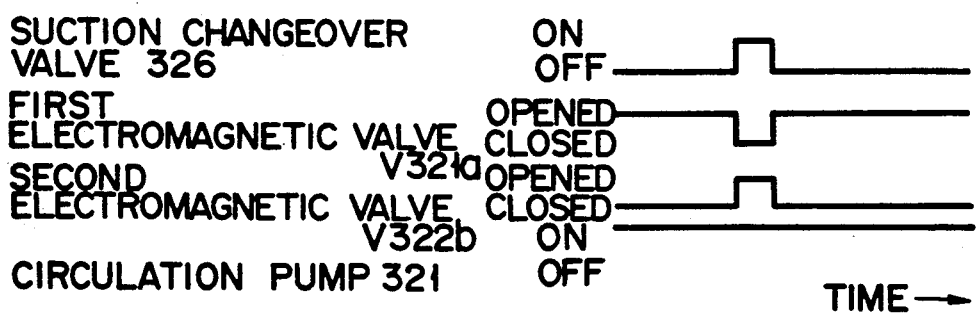
FIG. 18 is a time chart showing the relation among valves, detected pressures of a pressure sensor relating to a pump, and operations of electromagnetic changeover valves.

FIGS. 17 and 18 show a second variation of the fourth embodiment according to the present invention. When suction is carried out through the sucking passage 325 while supplying air through the nozzle 7 to form the air curtain in front of the viewing window 6 as seen in the case of the fourth embodiment and its first variation, circulation-air is also sucked via the sucking passage 325 to thereby decrease the amount of fluid which must be sucked. This second variation is intended to eliminate the drawback.

A first air supply passage 313a is connected to the air supply pump 37 at its one end and to the air/water changeover valve 318 at its other end. The air supply passage 314 which serves to supply water is branched from the first air supply passag 313a and communicated with the water supply tank 16. A first water supply passage 315a is connected to the water supply tank 16 at its one end and to the air/water changeover valve 318 at its other end. Second air and water supply passages 313b and 315b are connected to the air/water changeover valve 318. The second air and water supply passages 313b and 315b are combined with each other at the front portion of the inserting section and communicated with the air/water supply passage 316, which is connected to and communicated with the nozzle 7 at the front end of the inserting section.

The first sucking passage 323 is connected to the suction pump 39 at its one end and communicated with the sucking vessel 17 at its other end. A second sucking passage 325a is connected to the sucking vessel 17 at its one end and to the suction changeover valve 326 at its other end. Further, a third sucking passage 325b is connected to the suction changeover valve 326 at its one end and opened at the front end of the inserting section at its other end. The circulation-sucking passage 328 is branched from the third sucking passage 325b and communicated with a circulation-sucking vessel 310a. A circulation pump 321 is also connected to the circulation-sucking vessel 310a. The first circulation-air supply passage 319a is connected to the discharge side of the circulation pump 321 at its one end and to the second circulation-air supply passage 319b via a first electromagnetic valve 321 at its other end. Further, the second circulation-air supply passage 319b is connected to the second air supply passage 313b. An air supply passage 319c which serves to pressurize a circulation water supply vessel 310b to supply water is branched from the first circulation-air supply passage 319a. Further, a first circulation water supply passage 345a is connected to the circulation water supply vessel 310b at its one end and to second circulation-water supply passage 345b via a second electromagnetic valve 322 at its other end. The second circulation-water supply passage 345b is connected to the second water supply passage 315b.

Therefore, air supply is usually carried out as follows. Air supplied from the air supply pump 37 is sent to the air/water changeover valve 318 through the first air supply passage 313a. The passage in the air/water changeover valve 318 is changed over by finger to allow the air to be supplied through the nozzle 7 via the second air supply passage 313b and the air/water supply passage 316.

In the case of water supply, the pressure of the air supply pump 37 is added to the water supply tank 16 through the air supply passage 314 which serves to supply water, and pure water in the water supply tank 16 is thus forced into the first water supply passage 315a. The water thus forced into the passage 315a is passed through the passage which has been changed over in the air/water changeover valve 318 by finger, and supplied through the nozzle 7 via the second water supply passage 315b and the air/water supply passage 316.

Suction is conducted through the opening at the front end of the inserting section in such a way that negative pressure created by the suction pump 39 is transmitted to the first sucking passage 323, the sucking vessel 17, and the second sucking passage 325a, and then to the third sucking passage 325b through the passage which has been changed over in the suction changeover valve 326 by finger.

Circulation is carried out as follows. Fluid sucked by the circulation pump 321 through the third sucking passage 325b and the circulation-sucking passage 328 is sent into the circulation-sucking vessel 310a. The fluid thus sent into the vessel 310a is separated into liquid and air and only the air is sucked by the circulation pum 321 and sent to the front end of the inserting section through the first circulation-air supply passage 319a, the first electromagnetic valve V321a, the second circulation-air supply passage 319b and the second air supply passage 315b. The air thus reached the front end of the inserting section is then circulated through the nozzle 7.

Circulation during the suction process is carried out as shown by a time chart in FIG. 18. When suction is carried out while operating the suction changeover valve 326, the first electromagnetic valve V321a is closed while the second electromagnetic valve V322a is opened, thereby stopping the circulation-air supply but starting the circulation-water supply with extruding washing water in the vessel 310b.

A gas is far lighter than a liquid, and will likely be sucked more readily than the liquid. Therefore, when suction was carried out during the process of supplying circulation-air in the conventional cases, the circulation-air supplied through the nozzle 7 was sucked to thereby decrease the amount of fluid which must be sucked. When circulation-water is supplied only during the suction process as described above, however, almost no influence is added to the amount of fluid which must be sucked such as mucus and humor. The observation window can be still cleaned during the suction process.

Figure 19:
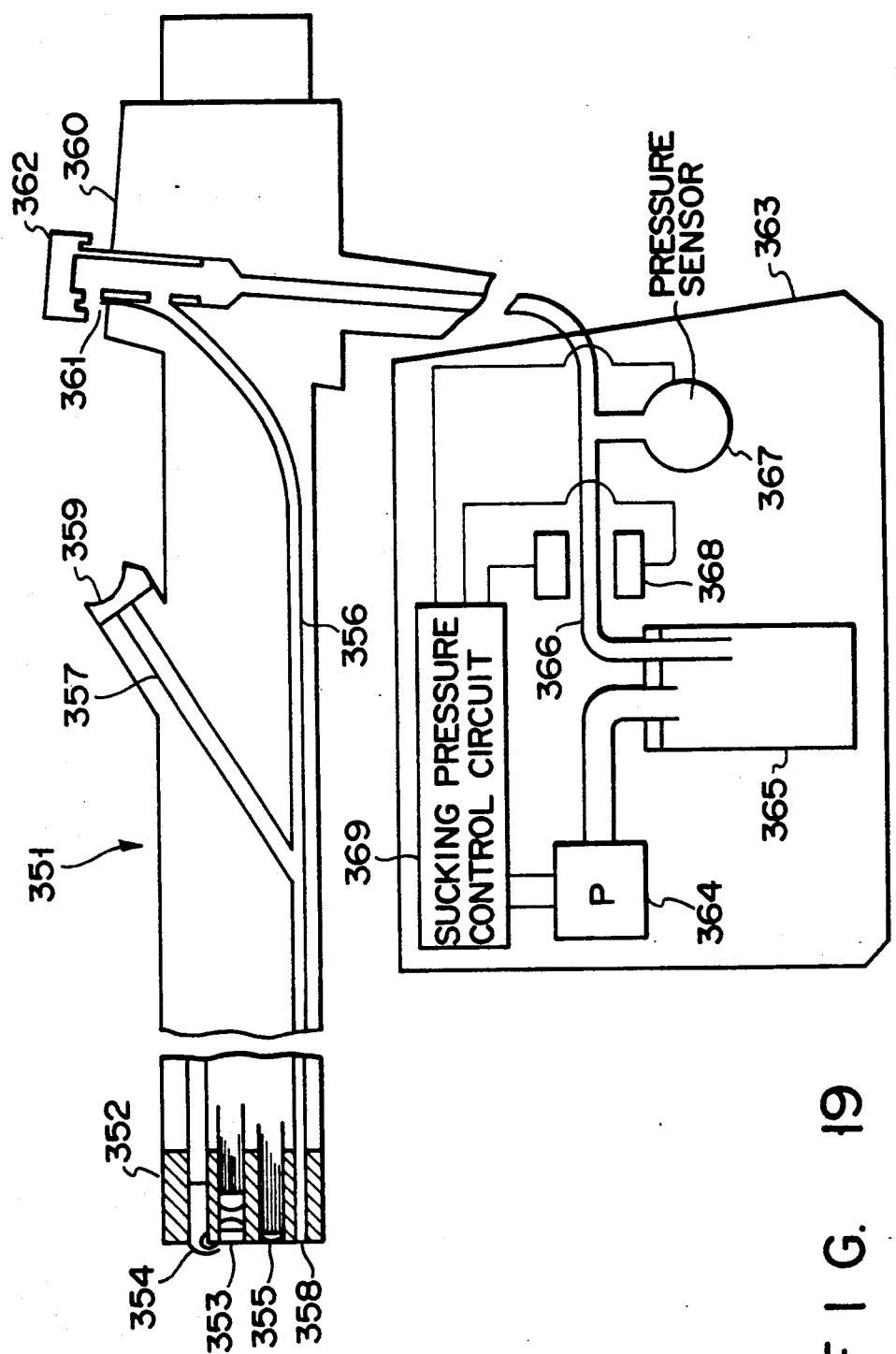
FIG. 19 schematically shows the endoscope device according to a third variation of the fourth embodiment of the present invention.

FIG. 19 shows a third variation of the fourth embodiment according to the present invention. This third variation can be embodied as an endoscope device capable of controlling suction pressure.

A front end 352 of an endoscope 351 which is inserted into the body cavity is provided with a viewing window 353, a nozzle 354 for washing the viewing window 353 clean, and a lighting window 355 and a sucking passage 356 is combined with a forceps inserting channel 357 and it has a channel opening 358 at the front end 352 of the endoscope 351. A forceps cap 359 which usually serves as a check valve is attached to the forceps inserting inlet of the channel 357. An operation section 360 of the endoscope 351 is provided with a suction operating button 362, which has a leak hole 361 through which leakage is carried out even when negative pressure is added to the sucking passage 356.

An endoscope suction means 363 is connected to the sucking passage 356 of the endoscope 351 which is arranged as described above. Reference numeral 364 represents a suction pump, which is communicated with sucking vessel 365 which is communicated with the sucking passage 356 through a transparent tube 366. The transparent tube 366 is provided with a pressure sensor 367 for detecting sucking pressure and an optical sensor 368 for detecting whether the matter sucked is liquid or gas. These optical and pressure sensors 368 and 367 are connected to a sucking pressure control circuit 369 which serves to control the output of the suction pump 364.

When the leak hole 361 of the suction operating button 362 is closed, therefore, the sucking passage 356 is communicated with the suction pump 364, which applies negative pressure to the sucking passage 356. The pressure sensor 367 sends signal "H" to the sucking pressure control circuit 369 and the optical sensor 368 sends signal "L" to it until fluid passes from the channel opening 358 of the front end 352 to the optical sensor 368. As the result, the control circuit 369 controls the suction pump 364 to conduct suction at low pressure. The optical sensor 368 sends signal "H" to the control circuit 369 when the fluid passes through the optical sensor 368. As the result, the control circuit 369 controls the suction pump 364 to conduct suction at high pressure.

When the pressure sensor 367 shows a value larger than a predetermined one in proportion to the sucking pressure, the suction pressure control circuit 369 causes the suction pump 364 to be communicated with atmospheric air.

The suction pump 364 can be controlled to make its pressure high, as described above, at the time when a large amount of fluid is to be sucked through the sucking passage 356. This enables suction time to be shortened. Further, when matters such as mucous membrances are sucked to close the channel opening 358, this opening can be made open again because the suction pump 364 is communicated with atmospheric air when the sucking pressure becomes higher than a certain threshold value. Furthermore, when the suction means 363 which serves to supply air and water at the same time is used, it can be arranged that excessive air is not supplied even when fluid is sucked.

Figure 20:
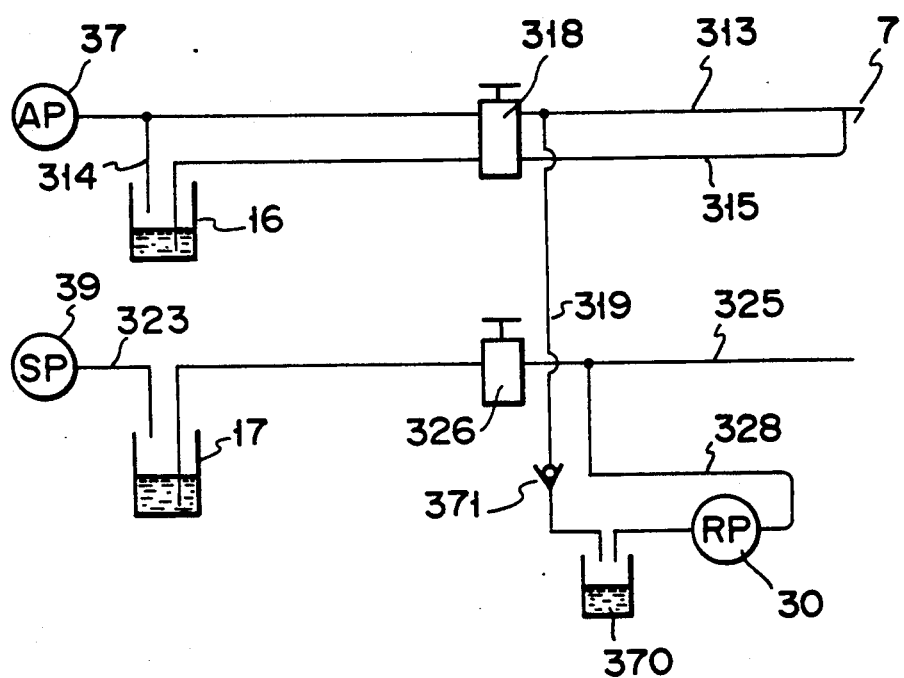
FIG. 20 shows a pipe system of the endoscope device according to a fourth variation of the fourth embodiment of the present invention.

FIG. 20 shows a fourth variation of the fourth embodiment according to the present invention.

A circulation surge tank 370 is provided instead of the circulation-sucking vessel 30. Further, the circulation pump 30 is attached to the circulation-sucking passage 328 on the way thereof and a check valve 371 is attached to the circulation-air supply passage 319 on the way thereof.

Normal air and water supplies are conducted in the same manner as in the fourth embodiment, but the re-opening of the channel opening and the sucking passage 325 is carried out as follows when matters such as mucous membrances or sordes are sucked to close the channel opening and the sucking passage. The circulation control means (not shown) controls the circulation pump 30 in such a way that the pump is stopped and again stopped after it is driven backward for an instant. The circulation pump 30 is caused by this control to suck air in the circulation surge tank 370 through the circulation-sucking passage 328 and to supply it from the passage 328 into the sucking passage 325, so that the matters adhering to the passage 325 can be pushed out of it by the pressure of air thus supplied.

When this control was conducted, that is, the circulation pump 30 was driven backward, the matters such as mucous membrances and liquids were sucked through the nozzle 7 and the nozzle 7 was jammed with the matters as the circulation pump 30 is driven backward. When the check valve 371 is attached to the circulation-air supply passage 319 between the circulation surge tank 370 and the air supply passage 313, however, the matters cannot be sucked through the nozzle 7 and an amount of air enough to eliminate the matters from the passage 325 can be supplied into it by the circulation surge tank 370.

In the embodiments described above, the nozzle opens to the observation window. Nonetheless, the nozzle need not projects from the distal end of the inserting section. Nor does it need to be bend toward the window. The nozzle is used as outlet port of the fluid supplied to it. Further, the gas can be supplied at any speed through the nozzle.

It should be understood that the present invention is not limited to the above-described embodiments and their variations and that various changes and modifications can be made without departing from the spirit and scope of the present invention.

What is claimed is:

1. An endoscope device comprising:
    an endoscope having a front end portion provided with a nozzle and a sucking opening;
    fluid supply means haivng a first passage connected to the nozzle for supplying a fluid to said nozzle;
    suction means having a second passage connected to said sucking opening;
    fluid circulating means having a fluid circulation pump attached to a third passage, said third passage being in fluid communication with both said first and second passages, said fluid circulation means circulating a sucked-in fluid through said third passage such that said sucked-in fluid is sucked in through said sucking opening and said second passage and expelled as a jet stream through said first passage and said nozzle; and
    a vessel attached to said third passage, said vessel being in fluid communication with a discharge side of said circulation pump, said vessel separating a gas from said sucked in fluid flowing through said third passage.

2. The endoscope device according to claim 1, further comprising:
    an observation window positioned at said front end portion of said endoscope; and wherein:
    said nozzle has an opening directed toward said observation window.

3. The endoscope device according to claim 1, further comprising:
    a by-pass passage for circulating said sucked in fluid flowing in said third passage without expelling said sucked in fluid through said nozzle; and
    change-over means for changing a fluid communication of said third passage to communicate with at least one of siad first and second passages and said by-pass passage.

4. The endoscope device according to claim 1, wherein:

said fluid supply means ocmprises a fluid supply pump in fluid communication with said first passage; and said suction means comprises a suction pump in fluid communication with said second passage.

5. The endoscope device according to claim 4, further comprising:

means for supplying a quantity of gas through said first passage; and means for stopping siad fluid circulation means after a supply of gas is started by a gas supply means.

6. The endoscope device according to claim 4, further comprising:

detector means for detecting an amount of fluid sucked in by said suction means; and means for adjusting a sucking force of said suction pump responsive to said amount of sucked in fluid detected by said detector means.

7. The endoscope device according to claim 4, further comprising means for driving said fluid circulation pump in a reverse direction when said sucking opening is closed.

8. The endoscope device according to claim 4, further comprising means for closing said third passage when said suction means is providing a sucking force.

9. The endoscope device according to claim 4, further comprising control means including stopper means for stopping said fluid circulating means during a sucking operation of said suction means.

10. The endoscope device according to claim 4, wherein said fluid supply means comprises means for supplying at least one of a quantity of air and a quantity of water to said first fluid passage.

11. The endoscope device according to claim 10, further comprising control emans for controlling said quantity of air to be circulated into said first passage by said circulation pump and for controlling said quantity of water to be supplied into said first passage by a water supply means.

12. The endoscope device according to claim 10, further comprising means for closing said third passage when said quantity of water is supplied into said first passage by a water supply means.

13. The endoscope device according to claim 10, further comprising means for driving both a water supply means and said fluid circulating means when said suction means is providing a sucking force.

* * * * *